United States Patent [19]

Troxler et al.

[11] 4,434,176

[45] Feb. 28, 1984

[54] USE OF 4-(2-BENZOYLOXY-3-TERT-BUTYLAMINO-PROPOXY)-2-METHYL-INDOLE FOR INDUCING BETA-ADRENOCEPTOR BLOCADE

[75] Inventors: Franz Troxler, Bottmingen; Fritz Seemann, Ettingen, both of Switzerland

[73] Assignee: Sandoz Ltd., Basle, Switzerland

[21] Appl. No.: 375,369

[22] Filed: May 6, 1982

Related U.S. Application Data

[62] Division of Ser. No. 138,901, Apr. 10, 1980, Pat. No. 4,340,541.

[30] Foreign Application Priority Data

Aug. 15, 1975 [CH] Switzerland ................. 10714/75

[51] Int. Cl.³ .............................................. A61K 31/40
[52] U.S. Cl. ................................................... 424/274
[58] Field of Search ........................................ 424/274

[56] References Cited

PUBLICATIONS

Dengler et al, "Die Therapeutische Anwendung B-sympathikolytischer Stoff", Rothburger Ges p., 7&8 May 1971, pp. 3-44.
Frishman et al., "Clinical Pharm. of the Beta-Adrenoceptor Blocking Drugs", pp. 21-23 and 42-46 Appelton-Cent.-Crofts, N.Y., N.Y. (1980).
Lee et al., "European Journal of Pharm.", 33 pp. 371-382 (1975).

Primary Examiner—Paul M. Coughlan, Jr.
Assistant Examiner—W. B. Springer
Attorney, Agent, or Firm—Gerald D. Sharkin; Robert S. Honor

[57] ABSTRACT

This invention provides compounds of formula I,

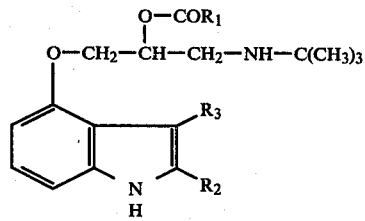

wherein
 $R_1$ is phenyl; phenyl monosubstituted with fluorine; phenyl mono- or disubstituted with chlorine; phenyl mono-, di- or trisubstituted with methyl or methoxy, secondary 1-phenoxyalkyl, the secondary alkyl residue of which is of 3 to 5 carbon atoms and in which the phenyl residue is unsubstituted or monosubstituted with chlorine, and
either $R_2$ is hydrogen,
and $R_3$ is methyl,
or $R_2$ is methyl
and $R_3$ is hydrogen or methyl, which are useful, for example, for treating coronary conditions.

5 Claims, No Drawings

USE OF 4-(2-BENZOYLOXY-3-TERT-BUTYLAMINO-PROPOXY)-2-METHYL-INDOLE FOR INDUCING BETA-ADRENOCEPTOR BLOCADE

This is a division of application Ser. No. 138,901, filed Apr. 10, 1980, U.S. Pat. No. 4,340,541 which in turn is a continuation of application Ser. No. 34,582, filed Apr. 30, 1979, now abandoned, which in turn is a continuation of application Ser. No. 711,906, filed Aug. 5, 1976, now abandoned.

The present invention relates to 4-(3-alkylaminopropoxy)-indole derivatives.

More particularly, this invention provides compounds of formula I,

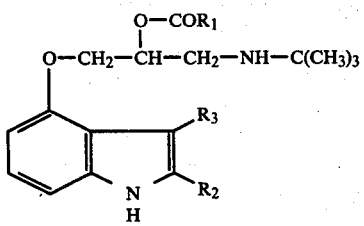

wherein
$R_1$ is phenyl; phenyl monosubstituted with fluorine; phenyl mono- or disubstituted with chlorine; phenyl mono-, di- or trisubstituted with methyl or methoxy, secondary 1-phenoxyalkyl, the secondary alkyl residue of which is of 3 to 5 carbon atoms and in which the phenyl residue is unsubstituted or monosubstituted with chlorine, and
either $R_2$ is hydrogen,
and $R_3$ is methyl,
or $R_2$ is methyl
and $R_3$ is hydrogen or methyl.

The substituent $R_1$ is preferably unsubstituted phenyl. When the phenyl residue bears more than one substituent, these substituents are preferably identical. When $R_1$ is secondary 1-phenoxyalkyl, the phenoxy residue is preferably substituted with chlorine. Preferred such radicals include 2-(p-chlorophenoxy)-2-propyl.

The compounds of formula I can, by virtue of the asymmetric carbon atom in the position β to the oxygen atom, exist in the form of optically active isomers or racemates. Of the (R) and (S) enantiomorphs, those which possess the (S)-configuration at the aforementioned carbon atom are preferred.

The invention also provides a process for the production of the compounds of formula I, comprising esterifying a compound of formula II,

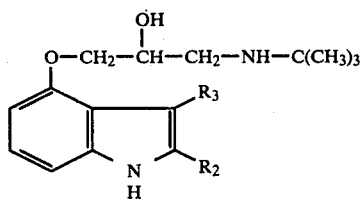

wherein $R_2$ and $R_3$ are as previously defined.

The process can be effected in manner analogous to known methods for the acylation of secondary alcohols, for example, by reaction with acid anhydrides or acid halides derived from acids of formula $R_1COOH$, wherein $R_1$ is as previously defined, preferably the anhydrides thereof. When the acylating agent to be used is an acid anhydride, the reaction may, for example, be effected at a temperature between ca. 0° and ca. 100° C., particularly in the presence of an excess of the acid anhydride. Prior to effecting the acylation, it is desirable to protonate the amino group, for example, by the addition of an acid, especially the acid $R_1COOH$, or to employ the compound of formula II in the form of an acid addition salt, for example, the hydrochloride. With acid halides, the acylation may preferably be effected at room temperature or at slightly elevated temperatures.

The process of the invention does not alter the configuration of the asymmetrically substituted carbon atom. Accordingly, when racemic starting materials are employed, racemic final products of formula I are obtained, and when optically active starting materials are employed, corresponding optically active final products are obtained.

The resulting compounds of formula I may be isolated and purified using conventional techniques.

Free base forms of the compounds of formula I may be converted into acid addition salt forms and vice versa in conventional manner.

The starting compounds are either known or may be produced in accordance with known processes, or in manner analogous to known processes.

In the following non-limitative Examples, all temperatures are indicated in degrees Centigrade and are uncorrected.

EXAMPLE 1

4-(2-Benzoyloxy-3-tert.butylaminopropoxy)-2-methyl-indole 26 g of Benzoic acid are dissolved, while heating, in 50 cc of hexamethylphosphoric acid triamide and 3.5 g of 1-tert.butylamino-3-(2-methyl-indole-4-yloxy)-2-propanol are added. After cooling, 3.0 g of benzoic acid anhydride are added and stirring is effected for 20 hours at room temperature. The resulting clear, yellow solution is poured onto ice, 0.5 liters of ether are added and stirring is effected for 2 hours. After making the liquid alkaline with concentrated ammonia, the ether phase is separated, shaken out with tartaric acid, made alkaline with caustic soda solution while cooling with ice and extracted with methylene chloride. After evaporating the solvent, the residue is crystallised with 1 mol of fumaric acid from methanol and acetone. M.p. of hydrogen fumarate form: 189°–191°.

In manner analogous to Example 1, but employing appropriate starting materials in approximately equivalent amounts, the following compounds of formula I can be obtained.

| Example | $R_1$ | $R_2$ | $R_3$ | M.P. |
|---|---|---|---|---|
| 2 | ⟨phenyl⟩ | H | $CH_3$ | Fu*:178–180° |
| 3 | ⟨phenyl⟩ | $CH_3$ | $CH_3$ | Fu*:185–187° |
| 4[1] | ⟨phenyl⟩ | $CH_3$ | H | HMo**:95° |

-continued

| Example | R₁ | R₂ | R₃ | M.P. |
|---|---|---|---|---|
| 5[2] |  | CH₃ | H | HMo**:95° |
| 6 |  | CH₃ | H | HMo**:91–94° |
| 7 | 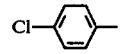 | CH₃ | H | HMo**:167–169° |
| 8 | 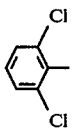 | CH₃ | H | HMo**:96–99° |
| 9 | 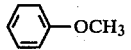 | CH₃ | H | HMo**:151–153° |
| 10 | 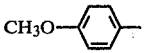 | CH₃ | H | HMo**:138–141° |
| 11 | 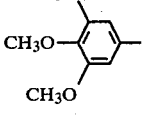 | CH₃ | H | HMo**:128–131° |
| 12 | 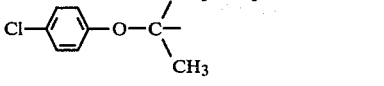 | CH₃ | CH₃ | H | HMo**:sinters at 85° |
| 13 | 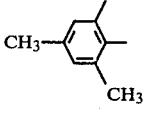 | CH₃ | H | HMo**:136–138° |
| 14 |  | H | CH₃ | — |
| 15 | 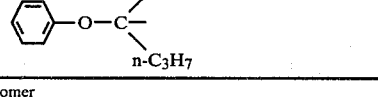 | CH₃ | CH₃ | — |

[1](S)-Enantiomer
[2](R)-Enantiomer
*Fu = Bis[base]fumarate
**HMo = Hydrogenmalonate The compounds of formula I are useful because they possess pharmacological activity in animals. In particular, the compounds are useful as α-adrenoceptor blocking agents, e.g. for the prophylaxis and therapy of coronary diseases, particularly in the treatment of Angina pectoris, in the hyperkinetic heart syndrome and conditions resulting from muscular hypertrophic subvalvular aortic stenosis, as indicated in standard tests, e.g. by an inhibition of the positive inotropic adrenaline effect in the spontaneously beating guinea pig atrium at a bath concentration of from 0.005 to 3 mg/liter in accordance with the method of K. Sammeli, Helv. Physiol. Acta. 25 CR 215-221 (1967); and in the infusion test in narcotized dogs at doses of approximately 0.02 to 1 mg/kg i.v., where they induce a strong, long lasting inhibition of the tachycardia and blood pressure lowering caused by isoproterenol.

For the abovementioned use, the dosage administered will, of course, vary depending on the compound employed, mode of administration and treatment desired. However, in general, satisfactory results are obtained with a daily dosage of from about 0.002 to about 3 mg/kg animal body weight, conveniently given in divided doses 2 to 4 times a day or in sustained release form. For the larger mammal, the total daily dosage is in the range of from about 1 to 200 mg, suitably from about 10 to about 200 mg, and dosage forms suitable for oral administration comprise from about 0.25 to about 100 mg, suitably from about 2.5 to about 100 mg, of the compound, admixed with a solid or liquid pharmaceutical carrier or diluent.

The compounds are furthermore useful as inhibitors of hyperlipoidemia induced by emotional stress and also as agents for the treatment and prophylaxis of myocardism as indicated in standard tests for showing inhibition of increased free fatty acid concentration due to mobilisation, and lipolysis, in blood, induced by emotional stress; for example, by an inhibition of glycerol release stimulated by isoproterenol (i) in vitro, e.g. at a concentration of about 0.1 to about 10 mg/l solution of the compounds in fat cells of the epididymal fat tissue of rats, the cells having been isolated in accordance with the method of M. Rodbell [J. Biol. Chem. 239, 375–80 (1964)] and (ii) in vivo, e.g. in rats on s.c. administration of from about 0.1 to about 1 mg/kg animal body weight of the compounds.

The compounds are furthermore useful as inhibitors of hyperglycemia induced by emotional stress and therefore as suppressants of appetite induced by emotional stress, as indicated in standard tests, e.g. by an inhibition of glucose release stimulated by isoproterenol in rats in vivo on s.c. administration of from about 0.1 to 1 mg/kg of animal body weight of the compounds.

For the abovementioned emotional stress uses for stress conditions the dosages will, of course, vary depending on the compound employed, mode of administration and treatment desired. However, in general, satisfactory results are obtained with a daily dosage of from about 0.01 to about 10 mg/kg animal body weight, conveniently given in divided doses 2 to 4 times a day or in sustained release form. For the larger mammal, the total daily dose is in the range of from about 1 to about 200 mg and dosage forms suitable for oral administration comprise from about 0.25 to about 100 mg of the components admixed with a solid or liquid pharmaceutical carrier or diluent.

The compounds are furthermore useful as antiarrhythmic agents, e.g. for the treatment of heart rhythm disorders, as indicated in standard tests, for example by a protection against cardiac arrhythmia induced by chloroform in mice on i.p. administration of from 10 to 50 mg/kg animal body weight of the compounds in accordance with the principles of J. W. Lawson [J. Pharmacol. Exp. Therap. (1968) 160,22–31].

For this use the dosage will, of course, vary depending on the compound employed, mode of administration and treatment desired. However, in general, satisfactory results are obtained with a daily dosage of from about 0.1 to 50 mg/kg animal body weight, conveniently given in divided doses 2 to 4 times a day or in sustained release form. For the larger mammal, the total daily dosage is in the range of from about 5 to 200 mg and dosage forms suitable for oral administration comprise from about 1 to 50 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the maleate, hydrogen maleate, fumarate, hydrogen fumarate, malonate, hydrogen malonate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutically acceptable carrier or diluent. Such compositions conveniently contain more than 1% by weight of the compound of formula I and may be in such forms as capsules.

The preferred compounds of this invention include 4-(2-benzoyloxy-3-tert.butylaminopropoxy)-2-methyl-indole.

The compounds of this invention exhibit more beneficial effects than would have been expected for such compounds.

We claim:

1. A pharmaceutical composition comprising 4-(2-benzoyloxy-3-tert.butylaminopropoxy)-2-methyl-indole or a pharmaceutically acceptable acid addition salt thereof, useful as a $\beta$-adrenoceptor blocker, for treating Angina pectoris, tachycardia or arrhythmia, in association with a pharmaceutically acceptable diluent or carrier.

2. A method of inducing $\beta$-adrenoceptor blockage in animals which comprises administering to an animal in need of such treatment a therapeutically effective amount of 4-(2-benzoyloxy-3-tert.butylaminopropoxy)-2-methyl-indole or a pharmaceutically acceptable acid addition salt thereof.

3. A method of treating Angina pectoris in animals which comprises administering to an animal in need of such treatment a therapeutically effective amount of 4-(2-benzoyloxy-3-tert.butylaminopropoxy)-2-methyl-indole or a pharmaceutically acceptable acid addition salt thereof.

4. A method of treating arrhythmia in animals which comprises administering to an animal in need of such treatment a therapeutically effective amount of 4-(2-benzoyloxy-3-tert.butylaminopropoxy)-2-methyl-indole or a pharmaceutically acceptable acid addition salt thereof.

5. A method for treating tachycardia in animals which comprises administering to an animal in need of such treatment a therapeutically effective amount of 4-(2-benzoyloxy-3-tert.butylaminopropoxy)-2-methyl-indole or a pharmaceutically acceptable acid addition salt thereof.

* * * * *